United States Patent
Wang

(10) Patent No.: US 10,744,219 B2
(45) Date of Patent: Aug. 18, 2020

(54) AIR FRESHENER COMPOSITION AND PREPARATION METHOD THEREOF

(71) Applicant: Jingning Wang, Huizhou (CN)

(72) Inventor: Jingning Wang, Huizhou (CN)

(73) Assignee: GUORUN BIOTECHNOLOGY (SHENZHEN) CO., LTD., Shenzhen (CN)

( * ) Notice: Subject to any disclaimer, the term of this patent is extended or adjusted under 35 U.S.C. 154(b) by 5 days.

(21) Appl. No.: 16/069,488

(22) PCT Filed: May 26, 2017

(86) PCT No.: PCT/CN2017/086159
§ 371 (c)(1),
(2) Date: Jul. 11, 2018

(87) PCT Pub. No.: WO2018/028276
PCT Pub. Date: Feb. 15, 2018

(65) Prior Publication Data
US 2020/0164096 A1    May 28, 2020

(30) Foreign Application Priority Data

Aug. 8, 2016 (CN) .......................... 2016 1 0644363

(51) Int. Cl.
| | | |
|---|---|---|
| *A61L 9/013* | (2006.01) | |
| *B01D 11/02* | (2006.01) | |
| *B01D 53/02* | (2006.01) | |
| *B01D 53/72* | (2006.01) | |
| *B01D 53/81* | (2006.01) | |
| *B01D 53/58* | (2006.01) | |

(52) U.S. Cl.
CPC .......... *A61L 9/013* (2013.01); *B01D 11/0211* (2013.01); *B01D 11/0288* (2013.01); *B01D 53/02* (2013.01); *B01D 53/58* (2013.01); *B01D 53/72* (2013.01); *B01D 53/81* (2013.01); *A61L 2209/21* (2013.01); *B01D 2253/20* (2013.01); *B01D 2257/406* (2013.01); *B01D 2257/708* (2013.01); *B01D 2257/7027* (2013.01)

(58) Field of Classification Search
CPC ....................................................... A61L 9/013
See application file for complete search history.

(56) References Cited

U.S. PATENT DOCUMENTS

2003/0024997 A1   2/2003   Welch et al.

FOREIGN PATENT DOCUMENTS

| CN | 101920029 | | 12/2010 |
|---|---|---|---|
| CN | 102178965 | A | 9/2011 |
| CN | 102908644 | A | 2/2013 |
| CN | 103041424 | A | 4/2013 |
| CN | 103550809 | A | 2/2014 |
| CN | 105056270 | A | 11/2015 |
| CN | 106039949 | A | 10/2016 |

OTHER PUBLICATIONS

Written Opinion of the International Searching Authority for Application No. PCT/Cn2017/086159 dated Aug. 16, 2017.

*Primary Examiner* — Arrie L Reuther
(74) *Attorney, Agent, or Firm* — Steven M. Shape; Dennemeyer & Associates, LLC

(57) ABSTRACT

The present invention relates to the field of air cleaning, and specifically discloses an air freshener composition. The air freshener composition comprises component A and component B, wherein a weight ratio of the component A to the component B is 1:0.5-3; the component A comprises, in parts by weight, 10-30 parts by weight of an active agent; 6-15 parts by weight of a carrier; 1-4 parts by weight of a pH regulator; and 0.01-0.2 part by weight of an antioxidant; the component B is a plant extract solution, wherein the plant extract solution comprises at least, in parts by weight: 5-30 parts by weight of an extract of a mixture of *Populus nigra* var. *italica*, grapefruit peels and eucalyptus leaves; 0.1-5 parts by weight of *Sophora flavescens* extract; 1-3 parts by weight of *Aloe vera* extract; 1-10 parts by weight of fresh orange peel extract; 0.5-3 parts by weight of *Nandina domestica* extract; 0.5-10 parts by weight of *Eucalyptus robusta* Smith extract; 1-8 parts by weight of *Robinia pseudoacacia* L. extract; 1-5 parts by weight of *Chrysanthemum morifolium* extract; and 0.1-2 parts by weight of artemisinin.

16 Claims, No Drawings

AIR FRESHENER COMPOSITION AND PREPARATION METHOD THEREOF

CROSS-REFERENCE TO RELATED APPLICATIONS

This is a 35 U.S.C. 371 National Stage Patent Application of International Application No. PCT/CN2017/086159, filed May 26, 2017, which claims priority to Chinese application 201610644363.8, filed Aug. 8, 2016, each of which is hereby incorporated by reference in its entirety.

FIELD OF THE INVENTION

The present invention relates to an air freshener composition, more particularly to an air freshener composition containing plant extracts, and still further relates to the field of B01D.

DESCRIPTION OF THE PRIOR ART

With the gradual improvement of living standards, the quality of the air environment is gradually reduced conversely, so the requirements for air purification are also getting higher and higher. There are a wide variety of air fresheners with different types of scents currently available on the market, most of which, however, are prepared by mixing organic compounds (e.g., aromatics and some monoterpenoids) with essences, which type of products can eliminate odors, but do not actually improve the air quality. Some synthetic air fresheners usually use phenol as the main component and are generally prepared into solid preparations. They are a class of chemical preparations synthesized by essences, ethanol and other ingredients, and contain formaldehyde, petroleum distillates, dichloro(benzene), mist catalysts, dimethyl ether and other propellants; a harmful substance called aerosol will be produced in the process of changing from liquid to gas. When in use, they dilute and cover up the odors by confusing one's sense of smell through giving off scents, and cannot purify the air, eliminate the microbes in the air, or are even air pollution sources themselves. Moreover, they also contain xylenes and ketones, which may cause neurasthenia, upper respiratory system diseases and other diseases, and even induce cancers when used in high doses.

Air fresheners using novel raw materials are in the product development phase, and no toxic side effects have been reported. Chlorine dioxide is basically nontoxic to the nuclei of higher animals and plant fibers, in particular, the reaction products resulting from disinfection and sterilization carried out by chlorine dioxide are basically nontoxic, so chlorine dioxide is an ideal chemical sanitizer which can be can be widely used in the sterilization and disinfection of families, hospitals, restaurants and the like.

Air fresheners using Chinese medicines not only should have the characteristics of killing all kinds of harmful microorganisms and eliminating toxic substances, but also should have advantages of being safe and efficient, having broad spectrum and no side effects, being easy to store and use, etc.

In view of the above problems, the present invention provides an air freshener composition which is safe and can also be used for a long time.

SUMMARY OF THE INVENTION

In order to solve the above problems, a first aspect of the present invention provides an air freshener composition, comprising component A and component B, wherein a weight ratio of the component A to the component B is 1:0.5-3;

the component A comprises, in parts by weight, 10-30 parts by weight of an active agent; 6-15 parts by weight of a carrier; 1-4 parts by weight of a pH regulator; and 0.01-0.2 part by weight of an antioxidant;

wherein the active agent comprises a compound containing at least two hydroxyl groups; and the carrier comprises an organic acid having 16-24 carbon atoms; and the component B is a plant extract solution, wherein the plant extract solution comprises at least, in parts by weight: 5-30 parts by weight of an extract of a mixture of *Populus nigra* var. *italica*, grapefruit peels and eucalyptus leaves; 0.1-5 parts by weight of *Sophora flavescens* extract; 1-3 parts by weight of *Aloe vera* extract; 1-10 parts by weight of fresh orange peel extract; 0.5-3 parts by weight of *Nandina domestica* extract; 0.5-10 parts by weight of *Eucalyptus robusta* Smith extract; 1-8 parts by weight of *Robinia pseudoacacia* L. extract; 1-5 parts by weight of *Chrysanthemum morifolium* extract; and 0.1-2 parts by weight of artemisinin.

In a preferred embodiment, the air freshener composition comprises component A and component B, wherein a weight ratio of the component A to the component B is 1:1-3;

the component A comprises, in parts by weight, 18-28 parts by weight of an active agent; 8-12 parts by weight of a carrier; 2-3 parts by weight of the pH regulator; and 0.1-0.2 part by weight of the antioxidant;

wherein the active agent comprises a compound containing at least two hydroxyl groups; and the carrier comprises an organic acid having 16-24 carbon atoms; and the component B is a plant extract solution, wherein the plant extract solution comprises at least, in parts by weight: 15-28 parts by weight of an extract of a mixture of *Populus nigra* var. *italica*, grapefruit peels and eucalyptus leaves; 1-3 parts by weight of *Sophora flavescens* extract; 1.5-3 parts by weight of *Aloe vera* extract; 3-8 parts by weight of fresh orange peel extract; 1-2 parts by weight of *Nandina domestica* extract; 3-10 parts by weight of *Eucalyptus robusta* Smith extract; 2-6 parts by weight of *Robinia pseudoacacia* L. extract; 2-4 parts by weight of *Chrysanthemum morifolium* extract; and 0.5-1.5 parts by weight of artemisinin.

In a preferred embodiment, the air freshener composition comprises component A and component B, wherein a weight ratio of the component A to the component B is 1:2;

the component A comprises, in parts by weight, 25 parts by weight of an active agent, 10 parts by weight of a carrier, 2.5 parts by weight of the pH regulator and 0.1 part by weight of the antioxidant;

the active agent comprises a compound containing at least two hydroxyl groups; and the carrier comprises an organic acid having 16-24 carbon atoms; and the component B is a plant extract solution, wherein the plant extract solution comprises at least, in parts by weight: 25 parts by weight of an extract of a mixture of *Populus nigra* var. *italica*, grapefruit peels and eucalyptus leaves; 2 parts by weight of *Sophora flavescens* extract; 3 parts by weight of *Aloe vera* extract; 7 parts by weight of fresh orange peel extract; 1.5 parts by weight of *Nandina domestica* extract; 8 parts by weight of *Eucalyptus robusta* Smith extract; 5 parts by weight of *Robinia pseudoacacia* L. extract; 4 parts by weight of *Chrysanthemum morifolium* extract; and 1 part by weight of artemisinin.

In a preferred embodiment, the active agent is selected from a combination of any one or more of ethylene glycol, propylene glycol, butylene glycol, polyethylene glycol, glycerol and 1,3,5-cyclohexanetriol.

In a preferred embodiment, the carrier is selected from a combination of any one or more of palmitic acid, stearic acid, arachidic acid and behenic acid.

In a preferred embodiment, a method for extracting the extract of the mixture of *Populus nigra* var. *italica*, grapefruit peels and eucalyptus leaves in the air freshener composition is as follows:

weighing and then crushing dried *Populus nigra* var. *italica* leaves, grapefruit peels and eucalyptus leaves at a weight ratio of 10:5:2, adding ethanol with a mass fraction of 95%, extracting a resultant mixture for 2-3 times using microwave heating after soaking for 3-10 h, filtering a resultant extract and concentrating a resultant filtrate under reduced pressure till no ethanol exists.

In a preferred embodiment, a method for extracting the *Nandina domestica* extract is as follows:

after weighing and crushing dried *Nandina domestica*, soaking resultant powder with white vinegar for 1-3 h, then adding 60% ethanol, extracting a resultant mixture for 2-3 times using microwave heating after soaking for 2-5 h, filtering a resultant extract and concentrating a resultant filtrate under reduced pressure till no white vinegar and ethanol exist.

In a preferred embodiment, in the air freshener composition, the component B further comprises 1 part by weight of an extract of a mixture of *Mentha spicata* L. and *Cannabis sativa* L.

A second aspect of the present invention provides a preparation method of the air freshener composition, the method comprising at least the following steps:

component A: adding a carrier into water, stirring a resultant mixture at 60-90° C. for 2-5 h, then adding corresponding parts by weight of an active agent, a pH regulator and an antioxidant, and stirring a resultant mixture at 40-60° C. for 1-3 h for use;

component B: mixing various plant extracts, and then stirring a resultant mixture at 20-40° C. for 1-2 h for use;

adding the component A to the component B, stirring a resultant mixture at 30-50° C. for 1-5 h, and evaporating the mixture to dryness to obtain an air freshener composition in the form of a paste solid.

A third aspect of the present invention provides an air freshener product comprising the air freshener composition described above.

DETAILED DESCRIPTION OF THE PREFERRED EMBODIMENTS

The content of the present invention can be more readily understood by reference to the following detailed description of the preferred embodiments of the present invention and examples included. Unless otherwise defined, all the technical and scientific terms used herein have the same meanings as commonly understood by one of ordinary skill in the art to which this invention belongs. When there are conflicts, the definitions in this description shall prevail.

As used herein, the term "prepared by" is synonymous with the term "comprising". As used herein, the terms "comprising", "including", "having", "containing" or any other variations thereof are intended to cover a non-exclusive inclusion. For example, a composition, a step, a method, a product or a device that comprise listed elements are not necessarily limited to only those elements, but may include other elements not expressly listed or elements inherent to such composition, step, method, product or device.

The conjunction "consisting of" excludes any element, step or component not identified. If used in a claim, this phrase will make the claim closed such that it excludes materials other than those described, except for usual impurities associated therewith. When the phrase "consisting of" appears in a clause of a claim body rather than immediately after the subject matter, it defines only elements described in the clause; and other elements are not excluded from the claim as a whole.

When amounts, concentrations or other values or parameters are indicated by ranges, preferred ranges or ranges defined by a series of preferred values of upper and lower limits, it should be understood to specifically disclose all ranges formed by any pair of any upper range limit or preferred value and any lower range limit or preferred value, regardless of whether the range is disclosed separately or not. For example, when a range of "1 to 5" is disclosed, the range described should be construed to include ranges of "1 to 4", "1 to 3", "1 to 2", "1 to 2 and 4 to 5", "1 to 3 and 5" and so on. When a range of numerical values is described herein, unless otherwise specified, the range is intended to include both end values and all integers and fractions within that range.

The singular forms include plural referents, unless the context clearly dictates otherwise. "Optional" or "any one" means that an item or an event described following it may or may not occur, and the description comprises the situation where the event occurred and the situation where the event did not occur.

An approximate language in the specification and claims is to be used to modify a number, meaning that the present invention is not limited to that particular number, but also comprises modifications that are acceptable and in close proximity to the number without resulting in a change in the related basic function. Accordingly, the use of "approximately", "about" or the like to modify a numerical value means that the present invention is not limited to the precise numerical value. In some instances, approximate terms may correspond to the accuracy of the instrument that measured the value. In the present specification and claims, the range limitations may be combined and/or interchanged, unless otherwise specified that these ranges include all sub-ranges encompassed thereby.

In addition, the indefinite articles "a" and "an" preceding an element or a component of the present invention have no limitations on the number of the elements or components required (i.e., the number of appearances). Hence, "a" or "an" should be read to include one or at least one, and the singular elements or components also include plural forms, unless the specified number obviously refers to singular forms.

The first aspect of the present invention provides an air freshener composition, comprising component A and component B, wherein a weight ratio of the component A to the component B is 1:0.5-3;

the component A comprises, in parts by weight, 10-30 parts by weight of an active agent; 6-15 parts by weight of a carrier; 1-4 parts by weight of a pH regulator; and 0.01-0.2 part by weight of an antioxidant;

the active agent comprises a compound containing at least two hydroxyl groups; and the carrier comprises an organic acid having 16-24 carbon atoms; and the component B is a plant extract solution, wherein the plant extract solution comprises at least, in parts by weight: 5-30 parts by weight of an extract of a mixture of *Populus nigra* var. *italica*, grapefruit peels and eucalyptus leaves; 0.1-5 parts by weight of *Sophora flavescens* extract; 1-3 parts by weight of *Aloe vera* extract; 1-10 parts by weight of fresh orange peel extract; 0.5-3 parts by weight of *Nandina domestica* extract; 0.5-10 parts by weight of *Eucalyptus robusta* Smith extract; 1-8 parts by weight of *Robinia pseudoacacia* L. extract; 1-5 parts by weight of *Chrysanthemum morifolium* extract; and 0.1-2 parts by weight of artemisinin.

Component A

In the present invention, the "component A" comprises 10-30 parts by weight of an active agent, 6-15 parts by weight of a carrier, 1-4 parts by weight of the pH regulator, and 0.01-0.2 part by weight of the antioxidant.

The active agent comprises a compound containing at least two hydroxyl groups, and examples thereof can include:

a combination of any one or more of ethylene glycol, propylene glycol, butylene glycol, polyethylene glycol, glycerol and 1,3,5-cyclohexanetriol.

The carrier comprises the organic acid having 16-24 carbon atoms, and examples thereof can include: palmitic acid, heptadecanoic acid, stearic acid, nonadecanoic acid, arachidic acid, heneicosanoic acid, behenic acid, tricosanoic acid and lignoceric acid.

In a preferred embodiment, the carrier is selected from a combination of any one or more of palmitic acid, stearic acid, arachidic acid and behenic acid.

Examples of the pH regulator can include a combination of any one or more of sodium hydroxide, potassium hydroxide, calcium hydroxide, sodium bicarbonate and disodium hydrogen phosphate.

Examples of the antioxidant can include: specific examples as an additive can include vitamin E acetate, phenolic antioxidants, phosphorus-containing antioxidants, sulfur-containing antioxidants and other various antioxidants; hindered amine thermal stabilizers and other various thermal stabilizers; inorganic antimicrobial agents, organic antimicrobial agents, mildew preventive agents and so on.

Examples of phenolic antioxidants include, but are not limited to any one of 1-hydroxy-3-methyl-4-isopropylbenzene, 2,6-di-t-butylphenol, 2,6-di-t-butyl-4-ethylphenol, 2,6-di-t-butyl-p-cresol, 2,6-di-t-butyl-4-n-butylphenol, 4-hydroxymethyl-2,6-di-t-butylphenol, t-butylhydroxyanisole, 2-(1-methylcyclohexyl)-4,6-dimethylphenol, 2,4-dimethyl-6-t-butylphenol, 2-methyl-4,6-dinonylphenol, 2,6-di-t-butyl-α-dimethylamino-p-cresol, 2,4,6-tri-t-butylphenol, 6-(4-hydroxy-3,5-di-t-butylanilino)-2,4-bis(octylthio)-1,3,5-triazine, 4,6-bis(4-hydroxy-3,5-di-t-butylphenoxy)-2-n-octylthio-1,3,5-triazine, methyl β-(3,5-di-t-butyl-4-hydroxyphenyl)propionate, n-octadecyl β-(4-hydroxy-3,5-di-t-butylphenyl)propionate, styrenated phenol, 4,4'-dihydroxybiphenyl, butylated octylated phenol, butylated styrenated cresol, 2,2'-methylenebis(4-methyl-6-t-butylphenol) or 2,2'-methylenebis(6-t-butyl-4-cresol), 2,2'-methylenebis(4-ethyl-6-t-butylphenol), 2,2'-methylenebis(4-methyl-6-cyclohexylphenol), 4,4'-methylenebis(2,6-di-t-butylphenol), 2,2'-methylenebis(6-α-methylbenzyl-p-cresol), 1,1-bis(4-hydroxybenzene)cyclohexane, 2,2'-methylenebis[4-methyl-6-(α-methylcyclohexyl)phenol] or 2,2'-dihydroxy-3,3'-di(α-methylcyclohexyl)-5,5'-dimethyl-diphenylmethane, 1,3,5-trimethyl-2,4,6-tris(3,5-di-t-butyl-4-hydroxybenzyl)benzene, 1,1,3-tris(2-methyl-4-hydroxy-5-t-butylphenyl)butane, pentaerythritol tetrakis[3-(3'5-di-t-butyl-4'-hydroxyphenyl)propionate], 4,4'-thiobis(6-t-butyl-3-methylphenol) or 4,4'-thiobis(6-t-butyl-m-cresol), 4,4'-thiobis(2-methyl-6-t-butylphenol) or 4,4'-thiobis(6-t-butyl-o-cresol), 2,2'-thiobis(4-methyl-6-t-butylphenol), hexanediol bis[β-(3,5-di-t-butyl-4-hydroxyphenyl)propionate], ethyl 2,2'-thiobis[3,-(3,5-di-t-butyl-4-hydroxyphenyl)propionate], N,N'-hexamethylenebis(3,5-di-t-butyl-4-hydroxyphenylpropionaniide), 1,3,5-tris(4-t-butyl-3-hydroxy-2,6-dimethylbenzyl) 1,3,5-triazine-2,4,6-(1H,3H,5H)-trione, 1,3,5-tris(3,5-di-t-butyl-4-hydroxybenzyl)s-triazine-2,4,6-(1H,3H,5H)-trione or tris(3,5-di-t-butyl-4-hydroxybenzyl)isocyanurate, tris[β-(3,5-di-t-butyl-4-hydroxyphenyl)propionyloxyethyl]isocyanurate, bis[3,3-bis(3'-t-butyl-4'-hydroxyphenyl)butyric acid]glycol ester, 1,1'-thiobis(2-naphthol), bis(3,5-di-t-butyl-4-hydroxybenzyl) sulfide, 2,5-di-t-butylhydroquinone, 2,5-di-t-amylhydroquinone, di-octadecyl 3,5-di-t-butyl-4-hydroxybenzyl phosphate, diethyl 3,5-di-t-butyl-4-hydroxybenzyl phosphate, triethylene glycol bis-3-(3-t-butyl-4-hydroxy-5-methylphenyl)propionate and hydroquinone dibenzyl ether.

Examples of phosphite antioxidants include, but are not limited to any one of triphenyl phosphite, tris(nonylphenyl)phosphite, triisooctyl phosphite, triisodecyl phosphite, phenyl diisodecyl phosphate, trilauryl trithiophosphite, trilauryl phosphite, trioctadecyl phosphite, diisodecyl pentaerythritol diphosphite, distearyl pentaerythritol diphosphite, 4,4'-butylidenebis[(3-methyl-6-t-butylphenyl)ditridecyl phosphite], diphenyl isooctyl phosphite, phenyl diisooctyl phosphite, diphenyloctyl phosphite, diphenylisodecyl phosphite, dioctyl phosphite, dilauryl phosphite, dimethyl phosphite, dioleyl phosphite, didecyl phosphite, dibutyl phosphite, ditridecyl phosphite, dimyristyl phosphite, triethyl phosphite, tributyl phosphite, triisopropyl phosphite, trioctyl phosphite or tris(2-ethylhexyl)phosphite, phenylbis(nonylphenyl)phosphite, diphenyl nonylphenyl phosphite and tris(2,4-di-t-butylphenyl)phosphite.

Examples of sulfur-containing ester antioxidants include, but are not limited to any one of dilauryl thiodipropionate, distearyl thiodipropionate or dioctadecyl thiodipropionate, dioctadecyl β,β'-thiodibutyrate, lauryl octadecyl thiodipropionate, ditridecyl thiodipropionate and ditetradecyl thiodipropionate.

Component B

The component B is a plant extract solution, wherein the plant extract solution comprises at least, in parts by weight: 5-30 parts by weight of an extract of a mixture of *Populus nigra* var. *italica*, grapefruit peels and *Eucalyptus robusta* Smith; 0.1-5 parts by weight of *Sophora flavescens* extract; 1-3 parts by weight of *Aloe vera* extract; 1-10 parts by weight of fresh orange peel extract; 0.5-3 parts by weight of *Nandina domestica* extract; 0.5-10 parts by weight of *Eucalyptus robusta* Smith extract; 1-8 parts by weight of *Robinia pseudoacacia* L. extract; 1-5 parts by weight of *Chrysanthemum morifolium* extract; 0.1-2 parts by weight of artemisinin; and 0.5-3 parts by weight of matrine.

*Populus nigra* var. *italica*

In the present invention, the "*Populus nigra* var. *italica*", also known as the Italian poplar, is a large deciduous tree with long oval crown and taupe bark and being lobed. The leaf blade is triangular, cordate at the base, has 2-4 glandular points, dark green in color and thick in leaf texture, and the leaf length is slightly larger than width. The petiole is flat.

Grapefruit Peels.

In the present invention, the "grapefruit peel" is the peel of pomelo, a plant belonging to Rutaceae. The peels are harvested at late fall and early winter and cut into dried ones with 5-7 petals. The peel after extension is about 25-32 cm in diameter, and each petal is 10-13 cm in length, 5-7 cm in width and 0.5-1 cm in thickness. The edge of the peel is slightly curled inward; the outer surface is yellowish-brown or yellowish and sometimes slightly golden yellow, very rough and has many concave dots and protruding oil spots; and the inner surface is white and slightly cottony. The peel is soft in texture and has a strong aroma of grapefruit.

Eucalyptus Leaves.

In the present invention, the "eucalyptus leaf" is also known as *Eucalyptus robusta* Smith leaf, *Eucalyptus globulus* leaf and Yangcaoguo leaf. The leaf is sickle-shaped and lanceolate, 8-30 cm long and 2-7 cm wide; the leaf is leathery and thick; the leaf end is tip, the leaf end is tip, and the leaf base is asymmetric and entire; and the petiole is short, 1-3 cm long, flat and twisted. The surface is yellow-green and glabrous, has many reddish-brown cork spots, is light-permeable and shows numerous transparent dots (oil chambers). The leaf has pinnate veins, and the ends of the lateral veins are joined at the leaf margin, forming vein patterns parallel with the leaf margin. When kneaded, the leaf has a slight aroma. It tastes slightly bitter and cold. Leaves that are large, complete, and have less petioles and no impurities are better.

Macrocarpal A, macrocarpal B, macrocarpal C, macrocarpal D, macrocarpal E, and n-tritriacontane-16,18-dione are isolated from the leaves. The leaves and the buds contain euglobal. The leaves also contain flavonoids: quercetol (i.e., quercetin), querictrin, rutin, hyperoside, quercetol-3-glucoside, and gallic acid, caffeic acid, ferulic acid, gentisic acid and protocate-chuic acid. The foliar wax contains 5,4-dihydroxy-7-methoxy-6-methylflavone, chrysin, eucalyptin, 8-demethyleu-calyptin and 4,5-dihydroxy-7-methoxy-6,8-dimethylflavone (sideroxylin). The volatile oils in the leaves mainly contain cineole, and further contain caryophyllene. Tritriacontane-16,18-dione, 3-O-methylellagic acid-4-rhamnoside, ellagic acid and ellagitannin are isolated from the bark and xylem.

In a preferred embodiment, a method for extracting the extract of the mixture of *Populus nigra* var. *italica*, grapefruit peels and eucalyptus leaves is as follows:

weighing and then crushing dried *Populus nigra* var. *italica* leaves, grapefruit peels and eucalyptus leaves at a weight ratio of 10:5:2, adding ethanol with a mass fraction of 95%, extracting a resultant mixture for 2-3 times using microwave heating after soaking for 3-10 h, filtering a resultant extract and concentrating a resultant filtrate under reduced pressure till no ethanol exists.

Microwaves are electromagnetic waves with frequencies in the range of about 300 MHz-300 GHz (i.e., wavelengths in the range of 100 cm-1 mm), which lie between the electromagnetic spectrum (light waves) and radio waves. Microwave is a very special electromagnetic wave band. Its performance is similar to that of sunlight. The wave speed is the same as the speed of light, both $3\times10^8$ m/s. The wavelength is 12.24 cm, and the oscillation frequency is 2.45 billion times per second.

Microwave extraction, also known as microwave-assisted extraction, refers to a method by which a component to be tested is extracted from sample matrix mainly through heating the sample and its organic solvent with thermal effects of microwaves. From a macro perspective, actually, microwave extraction is mainly the heating effect of microwaves on the extraction solvent and the sample, that is, microwaves can penetrate the extraction solvent and the material to make the whole system more evenly heated. From a micro perspective, the electromagnetic field generated by microwaves accelerates the diffusion rate of the sample to the extraction solvent interface.

The mechanism of microwave extraction can be considered from two aspects. On the one hand, the electromagnetic field generated by microwaves accelerates the diffusion rate of the extracted component to the extraction solvent interface; when water is used as the solvent, water molecules rotate at high speed in the microwave field to the excited state, which is a high-energy and unstable state, or gasification of the water molecules enhances the driving force to extract the component; or the water molecules themselves release energy back to the ground state, the released energy is transferred to other substance molecules to accelerate their thermal motion and shorten the time the molecules of the extracted component diffuse from the sample to the extraction solvent interface, thereby increasing the extraction rate several times, while also reducing the extraction temperature, to maximize the extraction quality. On the other hand, microwave energy is a kind of non-ionizing radiation energy that causes molecular motion by ion migration and dipole rotation. When it acts on the molecules, it promotes the rotational motion of the molecules. If the molecule has a certain polarity at this time, they are instantaneously polarized under the action of microwave electromagnetic field and perform the polarity transformation motion at the rate of 2.45 billion times per second, which results in vibration and tearing of bonds as well as friction and collision between particles, promoting the active parts (polar parts) of the molecules to better contact and react, while rapidly generating a lot of heat. Due to the absorption of microwave energy, the temperature inside the cells rises rapidly, causing the pressure inside the cells to exceed the expansion capacity of the cell wall and rupturing the cells. The active ingredients within the cells flow freely, so that they are captured and dissolved by the extraction medium in a short period of time.

In a preferred embodiment, the method for extracting the extract of the mixture of *Populus nigra* var. *italica*, grapefruit peels and eucalyptus leaves is as follows:

weighing and then crushing dried *Populus nigra* var. *italica* leaves, grapefruit peels and eucalyptus leaves at a weight ratio of 10:5:2, adding ethanol with a mass fraction of 95%, extracting a resultant mixture for 2-3 times using microwave heating after soaking for 3-10 h, filtering a resultant extract and concentrating a resultant filtrate under reduced pressure till no ethanol exists.

*Sophora flavescens*

In the present invention, the "*Sophora flavescens*" is dried roots of *Sophora flavescens*, a plant belonging to Leguminosae. The roots are excavated at spring and fall, the root heads and small roots are removed, the residues are washed off and the roots are dried, or the roots are sliced while they are fresh and dried.

The roots are long cylindrical, often branched at the bottom, 10-30 cm long and 1-2 cm in diameter. The surface is gray-brown or yellow-brown, and has longitudinal wrinkles and long horizontal lenticels. The outer skin is thin, often cracked and anti-roll, easy to peel, and yellow and smooth at the peel. They are hard in texture, not easy to break and fibrous at the section. The slices are 3-6 mm in thickness. The section is yellowish white, has radial textures and cracks, and some may have concentric rings. The roots have a faint smell and taste very bitter.

Matrine, oxymatrine, N-oxysophocarpine, sophoridine, d-allomatrine, d-isomatrine, d-sophoranol, (+)sophoranol N-oxide, l-sophocarpine, l-sophoramine, d-N-methylcytisine, l-anagyrine and baptifoline are isolated from the roots of *Sophora flavescens*. The roots also contain a variety of flavonoids: kushenol A, kushenol B, kushenol C, kushenol D, kushenol E, kushenol F, kushenol G, kushenol H, kushenol I, kushenol J, kushenol K, kushenol L, kushenol M, kushenol N, kushenol O, kuraridin, kuraridinol, kurarinol, neokurarinol, norkurarinol, isokurarinone, formononetin, kurarinone, norkurarinone, methylkushenol C, l-maackiain, trifolirhizin and rtifolirhizin-6"-O-malonate, kushenin, isoanhydroicaritin, noranhydroicaritin, xanthohumol, isoxanthohumol and luteolin-7-glucoside. In addition, the roots also contain triterpenoid saponins: sophoraflavoside I, sophoraflavoside II, sophoraflavoside III, sophoraflavoside IV, soyasaponin I and a quinone compound kushequinone A. The aerial parts contain alkaloids: matrine, oxymatrine, d-allomatrine, isomatrine, sophoranol, sophoranol N-oxide, anagyrine, baptifoline, 1-N-methylcytisine, l-sophocarpine, l-sophoramine, d-N-oxysophocarpine, 1-Δ7-dehydrosophoramine, isosophocarpine, 1-13,14-dehydrosophoridine, d-9a-hydroxymatrine, 1-9a-hydroxysophocarpine, 1-9a-hydroxysophocarpine N-oxide, 1-7,8-dehydrosophoramine, 1-9a-hydroxysophoramine, dimer of N-methyleytisine, sophoridine and d-12-lehmannine. The aerial parts also contain 2-alkylchromone derivatives, in which 2-n-heneicosyl-5,7-dihydroxy-6,8-dimethylchromone and 2-n-tricosyl-5,7-dihydroxy-6,8-dimethylchromone are dominant, and 2-n-tridecyl-5,7-dihydroxy-6,8-dimethylchromone, 2-n-pentadecyl-5,7-dihydroxy-6,8-dimethylchromone, 2-n-heptadecyl-5,7-dihydroxy-6,8-dimethylchromone, 2-n-nonadecyl-5,7-dihydroxy-6,8-dimethylchromone and 2-n-pentacosyl-5,7-dihydroxy-6,8-dimethylchromone are also present.

In a preferred embodiment, a method for extracting the *Sophora flavescens* is as follows: taking 5 g of dried *Angelica sinensis*, crushing it into powder, adding 100 mL ethanol with a mass concentration of 80% at 40° C., heating a resultant solution to reflux for 2 hours, followed by ultrasonic extraction for 2-5 h for 5 times, combining extract liquids, filtering a resultant combined extraction liquid and concentrating the resultant filtrate till no ethanol exists.

*Aloe vera*

In the present invention, the "*Aloe vera*" is a drought-tolerant herb belonging to Liliaceae, mainly distributed in Africa and other places, has antimicrobial, anti-inflammatory and laxative effects, and commonly used in the treatment of liver heat, flatulence, constipation, headache, eczemas, stones and other diseases. Polysaccharides and anthraquinones are abundant in fresh *Aloe vera* and are the main active sites. The *Aloe vera* gel contains a large number of carbohydrate components, most of which are different types of glucomannas, in which acetylated mannan has a higher biological activity. Other monosacdcarides contained are common arabinose, galactose, glucose, mannose, rhamnose and so on. Anthraquinones are mainly distributed in the subcutaneous palisade tissue, in which aloin and aloe-emodin are dominant, ad some of them are combined with polysaccharides to form glycoproteins and some of them are present in the form of enzymes, such as hydroxy peptidase, peroxidase, cellulase and superoxide dismutase. *Aloe vera* also contains lactic acid, succinic acid, malic acid, p-coumaric acid, succinic acid and citric acid and the like.

In a preferred embodiment, a method for extracting the *Aloe vera* is as follows: washing and then chopping 20 g of *Aloe vera*, mixing the chopped *Aloe vera* evenly with processed honey, then heating the resultant mixture to 60° C. for 3 h, extracting the mixture with ultrasonic for 3-5 h for 3 times using water as the solvent after cooling down, combining resultant extraction liquids, and filtering the resultant combined extraction liquids to dryness.

The term "processed honey" refers to one prepared by placing honey in a pan, heating it to slow boiling, switching to slow fire, maintaining slight boiling, removing foam and floating wax, then filtering dead bees and impurities with a sieve or gauze, then pouring the residue into a pot, heating it to 100° C.-118° C., and quickly removing the product from the pan when the pot is filled with fish eye bubbles, it feels sticky with hand, and there is no long white silk between the fingers.

Fresh Orange Peel Extract

In the present invention, the main component of the "fresh orange peel" is a monocyclic terpene containing limonene (methacrylcyclohexene) as a main component, having a citrus (lemon) fruit flavor with a boiling point of 175.5-176° C. Lemon oil itself is insoluble in water, and miscible with water in any proportion after adding an active agent.

The fresh orange peels contain a large amount of vitamin C and essential oils. The orange peels contain volatile oils, the main components of which are limonene, citral, and Chuanchenpitong, hesperidin, inositol, vitamin BI and so on. They have a gentle stimulating effect on the digestive tract, and are conducive to the discharge of the gas in the gastrointestinal tract. They promote the secretion of gastric juice, and may relax the bronchi. Porridge decocted with orange peels has the power of regulating vital energy and dispelling phlegm, and has the efficacy of invigorating and nourishing the stomach. They can be used to reduce blood lipids, elevate the blood pressure or treat acute mastitis.

Currently, there are more than 30 substances that have been isolated from orange peels, in which flavonoids, monoterpenes, coumarins, carotenoids, propanols, acridones, glyceroglycolipids and the like are dominant.

Flavonoids: there are three types of flavonoids contained in citrus fruits. Type I is general flavonoids represented by rutin; Type II is flavanones (e.g., hesperidin and naringin) specially contained in citrus fruits; and Type III is special polymethoxy-containing flavonoids (e.g., tangeritin) that have not been found in other vegetables and fruits so far except for citruses.

Carotenoids: as is well-known, many vegetables and fruits contain carotenoids, which are important ingredients for human health. Researches on the physiological function and mechanism of carotenoids have been developing rapidly in recent years. China has also developed some health foods using such substances and realized industrialized production.

Coumarins: the coumarins contained in citruses are anti-cancer substances fully affirmed by scientists. The research results show that the anti-cancer function of coumarins is formed by two main ways: first, coumarins detoxify cancer substances by the action of detoxification enzymes; and second, coumarins antagonize the cancer substances to inhibit their metabolic activation. Both of the two effects mainly have an inhibitory effect on cancers at the initial stage.

Monoterpenes and triterpenoids: citruses contain a large number of terpenoids represented by limonene. Terpenes are substances constituting the unique aroma of citruses, and have the effect of calming the central nervous system of humans.

Limonin: limonin is the bitter ingredient of orange peels.

In a preferred embodiment, the preparation method of the fresh orange peel extract is as follows: blasting and crushing 15 g of fresh orange peels to 100-200 mesh, blending with 2-mercaptobenzothiazole, and extracting the resultant mixture with ethanol as the solvent.

*Nandina domestica.*

In the present invention, the "*Nandina domestica*", also known as Hongtianzhu, is a plant belonging to *Nandina*, Southern Berberidaceae, Dicotyledoneae, and grown in Jiangsu, Zhejiang and Shaanxi, Guangxi and other provinces and regions along China's Yangtze river basin, as well as in Japan and India. They are mostly grown near wet valleys, under sparse forest or in shrubs, as indicator plants of calcareous soil. They are cultivated in both north and south gardens. They prefer warm, humid and well-ventilated half-shade environment. They are well resistant to cold, and can be cultivated at open field in the south of the Yellow River. The ripe fruits are left on the branches for ornamental purposes, and the temperature needs to be maintained at about 10° C. Potted ones should be placed in a sunshelter for conservation at spring and summer. They can be tolerant to slightly alkaline soil. They have strong sprouting power, and are generally multi-trunk and tufty. They are evergreen shrubs.

Their roots and stems can clear away heat and remove dampness, and clear and activate the channels and collaterals.

In a preferred embodiment, the preparation method of the *Nandina domestica* extract is as follows: after weighing and crushing 10 g of dried *Nandina domestica*, soaking the resultant powder with white vinegar for 1-3 h, then adding 60% ethanol, extracting the resultant mixture for 2-3 times using microwave heating after soaking for 2-5 h, filtering the resultant extract and concentrating the resultant filtrate under reduced pressure till no white vinegar and ethanol exist.

*Eucalyptus robusta* Smith

In the present invention, the "*Eucalyptus robusta* Smith", also known as *Eucalyptus*, is the collective name of plants belonging to Angophora, Corymbia and *Eucalyptus*, Myrtaceae, and the countries of origin are Indonesia, Australia and other places.

Examples of the species of the "*Eucalyptus robusta* Smith" can include: *Eucalyptus globulus*, *Eucalyptus maidenii*, *Eucalyptus citriodora*, *Eucalyptus robusta*, *foliage Tongqianan*, *Eucalyptus urophylla*, *Eucalyptus grandis*, *Eucalyptus tereticornis* smith, *Eucalyptus globulus*, *Eucalyptus dunnii* Maiden, *Eucalyptus saligna* Smith, *Eucalyptus urophydis*, *Eucalyptus urophylla*×*E. camaldulensis*, *Eucalyptus camaldulensis*, *Eucalyptus dunnii* Maiden, etc.

The major components of the eucalyptus bark extract are pentacyclic triterpenes, such as ursone, betulinic acid (Huamusuan), oleanolic acid, ursolic acid, betulic acid, betulinic acid (Huamuzhisuan), betulonic acid, 3-β-O-trans-p-hydroxy-cinnamoyl-12-ene-28-oleanolic acid and 3-β-O-trans-p-hydroxy-cinnamoyl-2σ-hydroxy-12-ene-ursolic acid.

The main components of the eucalyptus leaf extract are 1,8-cineole, pinene, aromadendrene, cumaldehyde, pinocarveol, 1-acetyl-4-isopropylidene cyclopentene, etc. Rutin, quercetin (Hupigan), quercetin (Hupisu) and homoserine are also present. Eucalyptin has been also separated. Other ingredients in the eucalyptus leaves, such as terpenes, flavonoids, tannins, phloroglucinols and glycosides, also have abundant biological activities.

In the present invention, the *Eucalyptus robusta* Smith extract is extracted from a blend of *Eucalyptus robusta* leaves and eucalyptus bark at a weight ratio of 1:18; and the eucalyptus leaves are picked at spring from 3-year-old *Eucalyptus robusta*.

In a preferred embodiment, the preparation method of the *Eucalyptus robusta* Smith extract is as follows: weighing the powder of *Eucalyptus robusta* bark and *Eucalyptus robusta* leaves in blend at a weight ratio of 1:18, adding ethanol, extracting the resultant mixture for 2-3 times using microwave heating after soaking for 2-3 h, filtering the resultant extract and concentrating the resultant filtrate under reduced pressure till no ethanol exists.

*Robinia pseudoacacia* L.

In the present invention, the "*Robinia pseudoacacia* L.", also known as *Robinia pseudoacacia* or locust, is a deciduous tree belonging to *Robinia*, Leguminosae. The bark is taupe to dark brown, lobed to deep longitudinal split, thin and smooth. According to the classification of the varieties, the locusts are divided into *Robinia pseudoacacia* 'Bessouiana', *Robinia pseudoacacia* 'Frisia', *Robinia pseudoacacia* 'Tortuosa', *Robinia pseudoacacia* 'Pyramidalis', *Robinia pseudoacacia* 'Umbraculifera', *Robinia pseudoacacia* 'Stricta', *Robinia pseudoacacia* 'Decaisneana', *Robinia pseudoacacia* var. *inermis*, *Robinia pseudoacacia* var. *microphylla*, *Robinia pseudoacacia* 'upright', *Robinia pseudoacacia* 'yellow', *R. pseudoacacia* f. *umbraculifera*. *Robinia*×*ambigua* 'Decaisneana' and Hongsenhui.

In the present invention, the locust is extracted from a blend of *Robinia pseudoacacia* 'Frisia', *Robinia*×*ambigua* 'Decaisneana' and *Robinia pseudoacacia* 'Decaisneana' at a weight ratio of 1:1:50.

The locust extract is preferably extracted from the leaves and flowers of locust.

In a preferred embodiment, the preparation method of the locust extract is as follows:

(1) The leaves of *Robinia pseudoacacia* 'Frisia', the leaves of *Robinia*×*ambigua* 'Decaisneana' and the leaves of *Robinia pseudoacacia* 'Decaisneana' are blended at a weight ratio of 1:1:50, the resultant blend is washed, chopped, then moistened with ammonia water, ethanol is added, the resultant solution is refluxed for 1-3 hours, filtered while hot and concentrated till no ethanol exists to obtain the extract of locust leaves.

(2) The flowers of *Robinia pseudoacacia* 'Frisia', the flowers of *Robinia*×*ambigua* 'Decaisneana' and the flowers of *Robinia pseudoacacia* 'Decaisneana' are blended at a weight ratio of 0.5:0.8:1.2, the resultant blend is washed and chopped, honey is added, the solution is refluxed for 1-3 hours, filtered while hot and concentrated till no ethanol exists to obtain the extract of locust flowers.

The extract of locust leaves from step 1 is blended with the extract of locust flowers from step 2, ethanol is added, the resultant mixture is stirred for 2.5 hours under ultrasound and concentrated till no ethanol exists in order to obtain the locust extract.

*Chrysanthemum morifolium*

In the present invention, the "*Chrysanthemum morifolium*" is a perennial herb with a perennial root, belonging to *Chrysanthemum*, Compositae in plant taxonomy. According to the cultivation form, chrysanthemums are divided into spray *chrysanthemum*, single-stem *chrysanthemum*, *Dali chrysanthemum*, *Xuanya chrysanthemum*, *Yi chrysanthemum*, *Antou chrysanthemum*. Chrysanthemums are cool in nature, bitter and spicy in taste, and distribute to the liver and heart.

The chemical components of *chrysanthemum* are divided into volatile oils, flavonoids, phenolic acids and other ingredients.

The volatile oils are composed mainly of monoterpenes, sesquiterpenes and their oxygen-containing derivatives and aliphatic compounds, as well as handelin chrysanthelide, chrysanthemol, chrysanthetriol, indicumeneone, cis-spiroenol ether, trans-spiroenol ether, angeloylcumambrin B, angeloylajadin, arteglasin A, cumambrin A, ursolic acid, β-sitosterol and the like.

Flavonoids: the main ingredients are luteolingglucoside, linarin, luteolin, apigenin, acacetin-7-rhamnose glucoside, luteolin-7-glucoside, quercetins, apigenin-7-O-β-D-glucopyranoside, diosmetin-7-O-β-D-glucopyranoside, quercetin-3,7-di-O-β-D-glucopyranoside, eriodictyol-7-O-β-D-glucopyranoside, 1-phenyl-2,3-butanediol-3-O-β-D-glucopyranoside and hesperetin-7-O-β-D-pyranglucuronide.

Phenolic acids: included are 3-O-caffeoylquinic acid, 4-O-caffeoylquinic acid, 5-O-caffeoylquinic acid, 3,5-dicaffeoylquinine acid methyl ester, 3,5-dicaffeoylquinine acid, 3,5-di-cis-caffeoylquinine acid, 1,5-dicaffeoylquinine acid, 1,3-dicaffeoylquinine acid, chlorogenic acid and so on.

Other ingredients: in addition to the volatile oils, flavonoids and phenolic acids, chrysanthemums also contain various trace elements, such as Ca, Mg and Fe, as well as proteins, amino acids, cholines, stachydrines, purines, tannins, vitamins, chlorophyll, carotenoids, glyceryl behenate, palmitic acid, etc.

The *Chrysanthemum morifolium* extract can be extracted in many ways, such as reflux extraction, ultrasonic extraction, steam distillation, microwave extraction, tissue disruption extraction and supercritical carbon dioxide extraction.

In a preferred embodiment, the extraction method of the *Chrysanthemum morifolium* extract is as follows: weighing and chopping 5 g of *chrysanthemum*, adding ethanol, extracting the resultant mixture for 2-3 times using microwave heating after soaking for 2-3 h, filtering the resultant extract and concentrating the resultant filtrate under reduced pressure till no ethanol exists.

Artemisinin

In the present invention, the "artemisinin" is a colorless needle-like crystal extracted from *Artemisia annua*, a compound inflorescence plant, and has a chemical name of (3R,5aS,6R,8aS,9R,12S,12aR)-octahydro-3,6,9-trimethyl-3,12-epoxy-12H-pyrano[4,3-j]-1,2-benzodithia-10(3H)-one. Its molecular formula is $C_{15}H_{22}O_5$, belonging to a sesquiterpene lactone. The compound has a peroxy bond and 6-membered lactone ring, and has a 1,2,4-trioxane structural unit including a peroxide, which is very rare in nature. The molecule comprises seven chiral centers, characterized in that ring A and ring B are cis-connected, and isopropyl and the bridgehead hydrogen are in trans relationship. The preparation m.p. is 156-157° C., [a]D17=+66.3° (C=1.64 chloroform). The compound is easily soluble in chloroform, acetone, acetic acid, ethyl ester and benzene, soluble in ethanol and diethyl ether, slightly soluble in cold petroleum ether, and almost insoluble in water. Due to its special peroxy group, it is thermally unstable and susceptible to wet, hot and reducing substances to be decomposed.

In the present invention, the artemisinin is purchased from Shaanxi Sealong Bio-Chemical Co., Ltd.

In a preferred embodiment, the air freshener composition comprises component A and component B, wherein the weight ratio of the component A to the component B is 1:1-3;

the component A comprises, in parts by weight, 18-28 parts by weight of an active agent; 8-12 parts by weight of a carrier; 2-3 parts by weight of a pH regulator; and 0.1-0.2 part by weight of an antioxidant;

wherein the active agent comprises a compound containing at least two hydroxyl groups; and the carrier comprises an organic acid having 16-24 carbon atoms; and the component B is a plant extract solution, wherein the plant extract solution comprises at least, in parts by weight: 15-28 parts by weight of an extract of a mixture of *Populus nigra* var. *italica*, grapefruit peels and eucalyptus leaves; 1-3 parts by weight of *Sophora flavescens* extract; 1.5-3 parts by weight of *Aloe vera* extract; 3-8 parts by weight of fresh orange peel extract; 1-2 parts by weight of *Nandina domestica* extract; 3-10 parts by weight of *Eucalyptus robusta* Smith extract; 2-6 parts by weight of *Robinia pseudoacacia* L. extract; 2-4 parts by weight of *Chrysanthemum morifolium* extract; and 0.5-1.5 parts by weight of artemisinin.

In a preferred embodiment, the air freshener composition comprises component A and component B, wherein the weight ratio of the component A to the component B is 1:2;

the component A comprises, in parts by weight, 25 parts by weight of an active agent, 10 parts by weight of a carrier, 2.5 parts by weight of the pH regulator and 0.1 part by weight of the antioxidant;

wherein the active agent comprises a compound containing at least two hydroxyl groups; and the carrier comprises an organic acid having 16-24 carbon atoms; and the component B is a plant extract solution, wherein the plant extract solution comprises at least, in parts by weight: 25 parts by weight of an extract of a mixture of *Populus nigra* var. *italica*, grapefruit peels and eucalyptus leaves; 2 parts by weight of *Sophora flavescens* extract; 3 parts by weight of *Aloe vera* extract; 7 parts by weight of fresh orange peel extract; 1.5 parts by weight of *Nandina domestica* extract; 8 parts by weight of *Eucalyptus robusta* Smith extract; 5 parts by weight of *Robinia pseudoacacia* L. extract; 4 parts by weight of *Chrysanthemum morifolium* extract; and 1 part by weight of artemisinin.

In a preferred embodiment, in the air freshener composition, the component B further comprises 1 part by weight of an extract of a mixture of *Mentha spicata* L. and *Cannabis sativa* L.

*Mentha spicata* L.

In the present invention, the "*Mentha spicata* L." is also known as Lvbohe, Xiangbohe, Helanbohe, Qingbohe, Xianghuacai and Yuxiangcai. It is an upright perennial herb plant belonging to Lamiaceae, has an upright stem and purple or white flowers, and flowers from July to September. It may adapt to a wide temperature range, prefers humid environment and light, and is suitable for weak acid soil. Spearmint oil can be extracted from its stem and leaves by distillation.

Systematic studies are performed on the active site of *Mentha spicata* L., a plant belonging to *Mentha*, Lamiaceae. Solvent method and various chromatographic methods are used. Results: seven compounds are isolated and identified as ursane, 3-methoxy-4-methylbenzaldehyde, veratric acid, 5-hydroxy-6,7,3',4'-tetramethoxyflavone, diosmetin, 5,6,4'-trihydroxy-7,8,3'-trimethoxyflavone and daucosterol.

The plant contains an aromatic oil with an oil content of 0.6-0.7%, and the oil is called spearmint oil or Lvbohe oil. Its main component is caraway oyster mushroom ketone (with a content of 60-65%). The oil also contains limonene and cress hydrocarbon oil hydrocarbons. The oil is mainly used for candies, spices for toothpastes, and for medical use. Leaves, shoots or the whole plant can also be used in medicine to treat cold fever, cough, consumptive cough, cold, headache, pharyngalgia, neuropathic headache, flatulence, bruises, eyeache, epistaxis, Wu therapy (a method of treatment), whole body numbness and pediatric sore boil.

The whole plant (*Mentha spicata* L.) is hot, sweet and slightly warm. It can be used to expel wind and remove cold, relieve cough, and disperse swelling and resolve toxin. It can be used to treat cold, cough, stomach pain, abdominal distension, neuropathic headache; and used for external use for bruises, eyeache and pediatric sore boil.

*Cannabis sativa* L.

In the present invention, the "*Cannabis sativa* L." is also known as white hemp seed, winter hemp seed, hemp seed, etc., and is sweet, neutral, and non-toxic. *Cannabis sativa*, commonly known as hemp and also known as cold hemp, China grass, tall hemp, dew hemp, Chinahemp, etc., belongs to Cannabaceae and is a short sunshine, annual, palmately branched and mostly dioecious herb, has the characteristics of tolerance to infertility and resistance to stress, and is grown in a wide range of places. In terms of biology, it has the characteristics of preferring sunshine and a high efficiency of photosynthesis. It grows vigorously under long-day sunshine conditions and the plant height can reach as high as 3.5 m. *Cannabis sativa* can be divided into three types: for fibers, for medicines and for seeds.

Hemp seed oil is a yellowish-green, translucent oily liquid at room temperature and becomes yellow-brown upon exposure for a long time with a special scent of hemp seeds.

In common hemp seed oils, the oil content is 30%-40%, the ratio of linoleic acid to linolenic acid is close to 2.5, which ratio is the best one for fatty acids required by the human body, while the respective metabolic active products of linoleic acid and stearic acid are also very abundant in content. In the fatty acid composition of hemp seed oils, C16 and C18 fatty acids are dominant, in which the mass fraction of diunsaturated linoleic acid and triunsaturated linolenic acid is up to 85.80% with a high degree of unsaturation. Currently identified, the hemp seed oils contain 29 compounds, of which 18 are fatty acids, accounting for 99.12% of the total content, wherein there are 11 saturated fatty acids, in which palmitic acid, stearic acid and arachidic acid are dominant with contents of 8.81%, 2.76% and 0.59%, respectively, and wherein there are 7 unsaturated fatty acids, accounting for about 87% of the total content, in which monounsaturated fatty acids are palmitoleic acid, oleic acid and arachidonic acid with contents of 0.08%, 8.92% and 0.26%, respectively. Polyunsaturated fatty acids are respectively γ-linolenic acid, linolenic acid and linoleic acid (with contents of 0.61%, 24.42% and 52.32%, respectively) as well as eicosa-5,8,11,14,17-pentaenoic acid (with a content of 0.34%). The fat-soluble components of hemp seed oils also include four ketones, two alcohols and three hydrocarbon substances. In addition, 13 ingredients are also identified, including dimethyl butyric acid, heptanoic acid, 2-methylpentanoic acid and eicosa-5,8,11,14,17-pentaenoic acid as well as ketones, hydrocarbons and alcohols.

At this stage, there are many ways to extract hemp seed oils, such as aqueous enzymatic extraction, supercritical fluid extraction, solvent extraction and pressing.

In the present invention, the hemp seed oil is mainly extracted by aqueous extraction.

Main extraction steps in the present invention are as follows:

(1) Raw Material Pretreatment and Baking.

Hemp seeds are washed clean and then baked at a certain temperature and time, baking denatures proteins from soluble ones into insoluble ones, and the original organization is destroyed. The globulins change in the oil, to transform hydrophilic groups into an irregular distribution state and hydrophobic groups to the outside, and to allow the greases contained within the globulins to be exposed on the surface and aggregate. Therefore, baking is convenient for grease extraction.

Crushing

When using aqueous extraction to extract oils, hemp seeds need to be ground and crushed, so that the oil cells are sufficiently broken, thus water and the slurry are well mixed during water adding and oil mixing, so as to fully combine non-oil substances and water and completely extract the greases as much as possible and ensure the quality of the oils.

(3) Water Adding and Mixing

First of all, hemp seeds are crushed and then mixed with tap water having a certain temperature at a certain percentage, the mixture is fully stirred and mixed, and fully dispersed and dissolved in water. At this moment, greases exposed on the surface of hemp seeds are extracted, and then greases in the pulverized particles are further extracted. The homogenate is stirred at a certain temperature and stirring speed to maximize the extraction of the greases in the homogenate. During stirring at a constant temperature, water is immersed in the hemp seed particles and binds the hydrophilic proteins instead of the greases in the hemp seed cells, so that the greases are released from the slurry.

Centrifugal Separation.

The resulting slurry is centrifuged at 4000 r/min for 20 min to obtain an upper oil layer and a lower residue layer to obtain the hemp seed oil.

In a preferred embodiment, the extraction method of the extract of the mixture of *Mentha spicata* L. and *Cannabis sativa* L. is as follows: weighing and chopping 5 g of *Mentha spicata* L., adding hemp seed oil, soaking the *Mentha spicata* L. for 2-3 h and then adding ethanol with a mass concentration of 50%, then extracting the resultant mixture for 2-3 times using microwave heating, filtering the resultant extract and concentrating the resultant filtrate under reduced pressure till no ethanol exists.

The present inventors have unexpectedly found that the air freshener composition, which is compounded with component A and component B, can remove formaldehyde, benzene-based pollutants, ammonia-based pollutants and volatile organic compounds in the air very well. The present inventors speculate that the probable cause may be that tannin compounds, terpenoids, ketone compounds and the like can be obtained from the plant extract in the component B, and these substances can not only physically adsorb formaldehyde, benzene-based pollutants, ammonia-based pollutants and volatile organic compounds in the air, but also produce chemical adsorption force, so as to achieve the purpose of purifying the air. Moreover, the component A can be combined with the component B to further enhance the adsorption effect of the component B; meanwhile, the use time of the air purifier composition can also be elongated, and the long-term use effect can be achieved.

The second aspect of the present invention provides a preparation method of the air freshener composition, comprising at least the following steps:

component A: adding a carrier into water, stirring the resultant mixture at 60-90° C. for 2-5 h, then adding corresponding parts by weight of an active agent, a pH regulator and an antioxidant, and stirring the resultant mixture at 40-60° C. for 1-3 h for use;

component B: mixing various plant extracts, and then stirring the resultant mixture at 20-40° C. for 1-2 h for use;

adding the component A to the component B, stirring the resultant mixture at 30-50° C. for 1-5 h, and evaporating the mixture to dryness to obtain an air freshener composition in the form of a paste solid.

The third aspect of the present invention provides an air freshener product comprising the air freshener composition described above.

EMBODIMENTS

Embodiment 1

Embodiment 1 of the present invention provides an air freshener composition, characterized in that the air freshener composition comprises component A and component B, wherein the weight ratio of the component A to the component B is 1:0.5-3;

the component A comprises, in parts by weight, 10-30 parts by weight of an active agent; 6-15 parts by weight of a carrier; 1-4 parts by weight of a pH regulator; and 0.01-0.2 part by weight of an antioxidant;

wherein the active agent comprises a compound containing at least two hydroxyl groups; and the carrier comprises an organic acid having 16-24 carbon atoms; and the component B is a plant extract solution, wherein the plant extract solution comprises at least, in parts by weight: 5-30 parts by weight of an extract of a mixture of *Populus nigra* var. *italica*, grapefruit peels and eucalyptus leaves; 0.1-5 parts by weight of *Sophora flavescens* extract; 1-3 parts by weight of *Aloe vera* extract; 1-10 parts by weight of fresh orange peel extract; 0.5-3 parts by weight of *Nandina domestica* extract; 0.5-10 parts by weight of *Eucalyptus robusta* Smith extract; 1-8 parts by weight of *Robinia pseudoacacia* L. extract; 1-5 parts by weight of *Chrysanthemum morifolium* extract; and 0.1-2 parts by weight of artemisinin.

Embodiment 2

Embodiment 2 of the present invention is the same as Embodiment 1, except that the air freshener composition comprises component A and component B, wherein the weight ratio of the component A to the component B is 1:1-3;

the component A comprises, in parts by weight, 18-28 parts by weight of an active agent; 8-12 parts by weight of a carrier; 2-3 parts by weight of the pH regulator; and 0.1-0.2 part by weight of the antioxidant;

wherein the active agent comprises a compound containing at least two hydroxyl groups; and the carrier comprises an organic acid having 16-24 carbon atoms; and the component B is a plant extract solution, wherein the plant extract solution comprises at least, in parts by weight: 15-28 parts by weight of an extract of a mixture of *Populus nigra* var. *italica*, grapefruit peels and eucalyptus leaves; 1-3 parts by weight of *Sophora flavescens* extract; 1.5-3 parts by weight of *Aloe vera* extract; 3-8 parts by weight of fresh orange peel extract; 1-2 parts by weight of *Nandina domestica* extract; 3-10 parts by weight of *Eucalyptus robusta* Smith extract; 2-6 parts by weight of *Robinia pseudoacacia* L. extract; 2-4 parts by weight of *Chrysanthemum morifolium* extract; and 0.5-1.5 parts by weight of artemisinin.

Embodiment 3

Embodiment 3 of the present invention is the same as Embodiment 2, except that the air freshener composition comprises component A and component B, wherein the weight ratio of the component A to the component B is 1:2;

the component A comprises, in parts by weight, 25 parts by weight of an active agent, 10 parts by weight of a carrier, 2.5 parts by weight of the pH regulator and 0.1 part by weight of the antioxidant;

wherein the active agent comprises a compound containing at least two hydroxyl groups; and the carrier comprises an organic acid having 16-24 carbon atoms; and the component B is a plant extract solution, wherein the plant extract solution comprises at least, in parts by weight: 25 parts by weight of an extract of a mixture of *Populus nigra* var. *italica*, grapefruit peels and eucalyptus leaves; 2 parts by weight of *Sophora flavescens* extract; 3 parts by weight of *Aloe vera* extract; 7 parts by weight of fresh orange peel extract; 1.5 parts by weight of *Nandina domestica* extract; 8 parts by weight of *Eucalyptus robusta* Smith extract; 5 parts by weight of *Robinia pseudoacacia* L. extract; 4 parts by weight of *Chrysanthemum morifolium* extract; and 1 part by weight of artemisinin.

Embodiment 4

Embodiment 4 of the present invention is the same as Embodiment 1, except that the active agent is selected from a combination of any one or more of ethylene glycol, propylene glycol, butylene glycol, polyethylene glycol, glycerol and 1,3,5-cyclohexanetriol.

Embodiment 5

Embodiment 5 of the present invention is the same as Embodiment 1, except that the carrier is selected from a combination of any one or more of palmitic acid, stearic acid, arachidic acid and behenic acid.

Embodiment 6

Embodiment 6 of the present invention is the same as Embodiment 1, except that the method for extracting the extract of the mixture of *Populus nigra* var. *italica*, grapefruit peels and eucalyptus leaves is as follows:

weighing and then crushing dried *Populus nigra* var. *italica* leaves, grapefruit peels and eucalyptus leaves at a weight ratio of 10:5:2, adding ethanol with a mass fraction of 95%, extracting the resultant mixture for 2-3 times using microwave heating after soaking for 3-10 h, filtering the resultant extract and concentrating the resultant filtrate under reduced pressure till no ethanol exists.

Embodiment 7

Embodiment 7 of the present invention is the same as Embodiment 1, except that the method for extracting the *Nandina domestica* extract is as follows:

after weighing and crushing dried *Nandina domestica*, soaking the resultant powder with white vinegar for 1-3 h, then adding 60% ethanol, extracting the resultant mixture for 2-3 times using microwave heating after soaking for 2-5 h, filtering the resultant extract and concentrating the resultant filtrate under reduced pressure till no white vinegar and ethanol exist.

Embodiment 8

Embodiment 8 of the present invention is the same as Embodiment 1, except that the component B further comprises 1 part by weight of an extract of a mixture of *Mentha spicata* L. and *Cannabis sativa* L.

Embodiment 9

Embodiment 9 of the present invention provides a preparation method of the air freshener composition according to Embodiments 1-8, the method comprising at least the following steps:

component A: adding a carrier into water, stirring the resultant mixture at 60-90° C. for 2-5 h, then adding corresponding parts by weight of an active agent, a pH regulator and an antioxidant, and stirring the resultant mixture at 40-60° C. for 1-3 h for use;

component B: mixing various plant extracts, and then stirring the resultant mixture at 20-40° C. for 1-2 h for use;

and adding the component A to the component B, stirring the resultant mixture at 30-50° C. for 1-5 h, and evaporating the resultant mixture to dryness to obtain an air freshener composition in the form of a paste solid.

Embodiment 10

Embodiment 10 of the present invention provides an air freshener product comprising the air freshener composition according to Embodiments 1-8.

The present invention will now be described in detail by way of examples below. It is necessary to point out here that the following examples are only used for further description of the present invention and are not intended to limit the scope of protection of the present invention. Some non-essential improvements and adjustments made by those skilled in the art based on the above content of the present invention still fall within the scope of protection of the present invention.

In addition, unless otherwise stated, the raw materials used are all commercially available, and the following materials are used in parts by weight.

Example 1: (Small Scale)

Example 1 of the present invention provides an air freshener composition comprising component A and component B, wherein the weight ratio of the component A to the component B is 1:0.5;

the component A comprises, in parts by weight, 10 parts by weight of an active agent (the active agent is propylene glycol); 15 parts by weight of a carrier (the carrier is palmitic acid and stearic acid at a weight ratio of 2:1); 1 part by weight of a pH regulator (the pH regulator is sodium hydroxide); 0.01 part by weight of an antioxidant (the antioxidant is vitamin E acetate); and the component B is a plant extract solution, wherein the plant extract solution comprises, in parts by weight: 5 parts by weight of an extract of a mixture of *Populus nigra* var. *italica*, grapefruit peels and eucalyptus leaves; 0.1 part by weight of *Sophora flavescens* extract; 1 part by weight of *Aloe vera* extract; 1 part by weight of fresh orange peel extract; 0.5 part by weight of *Nandina domestica* extract; 0.5 part by weight of *Eucalyptus robusta* Smith extract; 1 part by weight of *Robinia pseudoacacia* L. extract; 1 part by weight of *Chrysanthemum morifolium* extract; and 0.1 part by weight of artemisinin.

The method for extracting the extract of the mixture of *Populus nigra* var. *italica*, grapefruit peels and eucalyptus leaves was as follows:

weighing 81 g of a dried mixture of *Populus nigra* var. *italica* leaves, grapefruit peels and eucalyptus leaves at a weight ratio of 10:5:2; adding 1 liter of ethanol with a mass fraction of 95%; extracting the resultant mixture for 3 times using microwave heating after soaking for 10 h; filtering the resultant extract and concentrating the resultant filtrate under reduced pressure till no ethanol exists.

The method for extracting the *Sophora flavescens* extract was as follows:

taking 5 g of dried *Angelica sinensis*, crushing it into powder, adding 100 mL ethanol with a mass concentration of 80% at 40° C., heating the resultant solution to reflux for 2 hours, followed by ultrasonic extraction for 5 h for 5 times, combining the resultant extracts, filtering the combined extract and concentrating the resultant filtrate till no ethanol exists.

The method for extracting the *Aloe vera* extract was as follows:

washing and then chopping 20 g of *Aloe vera*, mixing the chopped *Aloe vera* evenly with processed honey, then heating the resultant mixture to 60° C. for 3 h, extracting the mixture with ultrasonic for 3 h for 3 times using water as the solvent after cooling down, combining the resultant extracts, and filtering and then concentrating the combined extract to dryness.

The method for extracting the fresh orange peel extract was as follows:

blasting and crushing 15 g of fresh orange peels to 100-200 mesh, blending with 2-mercaptobenzothiazole, then adding 100 mL ethanol with a mass concentration of 50% at 30° C., heating the resultant solution to reflux for 2 hours, followed by ultrasonic extraction for 5 h for 3 times, combining the extracts, filtering the combined extract and concentrating the filtrate till no ethanol exists.

The method for extracting the *Nandina domestica* extract was as follows:

after weighing and crushing 10 g of dried *Nandina domestica*, soaking the resultant powder with white vinegar for 1 h, then adding ethanol with a mass concentration of 60%, extracting the resultant mixture for 3 times using microwave heating after soaking for 5 h, filtering the resultant extract and concentrating the resultant filtrate under reduced pressure till no white vinegar and ethanol exist.

The method for extracting the *Eucalyptus robusta* Smith extract was as follows:

weighing the powder of *Eucalyptus robusta* bark and *Eucalyptus robusta* leaves in blend at a weight ratio of 1:18, adding ethanol with a mass concentration of 80%, extracting the resultant mixture for 3 times using microwave heating after soaking for 3 h, filtering the resultant extract and concentrating the resultant filtrate under reduced pressure till no ethanol exists.

The method for extracting the *Robinia pseudoacacia* L. extract was as follows:

(1) The leaves of *Robinia pseudoacacia* 'Frisia', the leaves of *Robinia×ambigua* 'Decaisneana' and the leaves of *Robinia pseudoacacia* 'Decaisneana' were blended at a weight ratio of 1:1:50, the resultant blend was washed, chopped, and then moistened with ammonia water, ethanol with a mass concentration of 50% was added, the resultant solution was refluxed for 1 hour, filtered while hot and concentrated till no ethanol exists to obtain the extract of locust leaves.

(2) The flowers of *Robinia pseudoacacia* 'Frisia', the flowers of *Robinia×ambigua* 'Decaisneana' and the flowers of *Robinia pseudoacacia* 'Decaisneana' were blended at a weight ratio of 0.5:0.8:1.2, the resultant blend was washed and chopped, honey was added, the resultant solution was refluxed for 3 hours, filtered while hot and concentrated till no ethanol exists to obtain the extract of locust flowers.

(3) The extract of locust leaves from step 1 was blended with the extract of locust flowers from step 2, ethanol was added, the resultant mixture was stirred for 2.5 hours under ultrasound and concentrated till no ethanol exists in order to obtain the locust extract.

The method for extracting the *Chrysanthemum morifolium* extract was as follows:

weighing and chopping 5 g of *chrysanthemum*, adding ethanol with a mass concentration of 80%, extracting the resultant mixture for 3 times using microwave heating after soaking for 2 h, filtering the resultant extract and concentrating the resultant filtrate under reduced pressure till no ethanol exists.

A preparation method of the air freshener composition, the method comprising at least the following steps:

component A: adding a carrier into water, stirring the resultant mixture at 60° C. for 2 h, then adding corresponding parts by weight of an active agent, a pH regulator and an antioxidant, and stirring the resultant mixture at 40° C. for 3 h for use;

component B: mixing various plant extracts, and then stirring the resultant mixture at 40° C. for 1 h for use;

and adding the component A to the component B, stirring the resultant mixture at 50° C. for 5 h, and evaporating the mixture to dryness to obtain an air freshener composition in the form of a paste solid.

Example 2: (Large Scale)

Example 2 of the present invention provides an air freshener composition comprising component A and component B, wherein the weight ratio of the component A to the component B is 1:3;

the component A comprises, in parts by weight, 30 parts by weight of an active agent (the active agent is propylene glycol); 6 parts by weight of a carrier (the carrier is palmitic acid and stearic acid at a weight ratio of 2:1); 4 parts by weight of a pH regulator (the pH regulator is sodium hydroxide); and 0.2 part by weight of an antioxidant (the antioxidant is vitamin E acetate); and the component B is a plant extract solution, wherein the plant extract solution comprises at least, in parts by weight: 30 parts by weight of an extract of a mixture of *Populus nigra* var. *italica*, grapefruit peels and eucalyptus leaves; 5 parts by weight of *Sophora flavescens* extract; 3 parts by weight of *Aloe vera* extract; 10 parts by weight of fresh orange peel extract; 3 parts by weight of *Nandina domestica* extract; 10 parts by weight of *Eucalyptus robusta* Smith extract; 8 parts by weight of *Robinia pseudoacacia* L. extract; 5 parts by weight of *Chrysanthemum morifolium* extract; and 2 part by weight of artemisinin.

The methods for extracting various plant extracts in the component B and the air freshener composition were the same as those in Example 1.

Example 3: (Optimal Scale)

Example 3 of the present invention provides an air freshener composition comprising component A and component B, wherein the weight ratio of the component A to the component B is 1:2;

the component A comprises, in parts by weight, 25 parts by weight of an active agent (the active agent is propylene glycol); 10 parts by weight of a carrier (the carrier is palmitic acid and stearic acid at a weight ratio of 2:1); 2.5 parts by weight of a pH regulator (the pH regulator is sodium hydroxide); and 0.1 part by weight of an antioxidant (the antioxidant is vitamin E acetate); and the component B is a plant extract solution, wherein the plant extract solution comprises at least, in parts by weight: 25 parts by weight of an extract of a mixture of *Populus nigra* var. *italica*, grapefruit peels and eucalyptus leaves; 2 parts by weight of *Sophora flavescens* extract; 3 parts by weight of *Aloe vera* extract; 7 parts by weight of fresh orange peel extract; 1.5 parts by weight of *Nandina domestica* extract; 8 parts by weight of *Eucalyptus robusta* Smith extract; 5 parts by weight of *Robinia pseudoacacia* L. extract; 4 parts by weight of *Chrysanthemum morifolium* extract; and 1 part by weight of artemisinin.

The methods for extracting various plant extracts in the component B and the air freshener composition were the same as those in Example 1.

Example 4: (Optimal Scale+Extract of Mixture of *Mentha spicata* L. and *Cannabis sativa* L.)

Example 4 of the present invention provides an air freshener composition comprising component A and component B, wherein the weight ratio of the component A to the component B is 1:2;

the component A comprises, in parts by weight, 25 parts by weight of an active agent (the active agent is propylene glycol); 10 parts by weight of a carrier (the carrier is palmitic acid and stearic acid at a weight ratio of 2:1); 2.5 parts by weight of a pH regulator (the pH regulator is sodium hydroxide); 0.1 part by weight of an antioxidant (the antioxidant is vitamin E acetate); and the component B is a plant extract solution, wherein the plant extract solution comprises at least, in parts by weight: 25 parts by weight of an extract of a mixture of *Populus nigra* var. *italica*, grapefruit peels and eucalyptus leaves; 2 parts by weight of *Sophora flavescens* extract; 3 parts by weight of *Aloe vera* extract; 7 parts by weight of fresh orange peel extract; 1.5 parts by weight of *Nandina domestica* extract; 8 parts by weight of *Eucalyptus robusta* Smith extract; 5 parts by weight of *Robinia pseudoacacia* L. extract; 4 parts by weight of *Chrysanthemum morifolium* extract; 1 part by weight of artemisinin; and 1 part by weight of an extract of a mixture of *Mentha spicata* L. and *Cannabis sativa* L.

The method for extracting the extract of the mixture of *Mentha spicata* L. and *Cannabis sativa* L. was as follows:

The steps for extracting the *Cannabis sativa* L. extract were as follows:

(1) Raw Material Pretreatment and Baking 300 g of *Cannabis sativa* L. was washed and then baked at 100° C. for 8 hours.

(2) Crushing

The baked *Cannabis sativa* L. was crushed.

(3) Water Adding and Mixing 1 liter of water was added to the crushed *Cannabis sativa* L., the temperature was raised to 80° C., and the mixture was stirred for 4 hours.

(4) Centrifugal Separation

The resulting slurry was centrifuged at 4000 r/min for 20 min to obtain an upper oil layer and a lower residue layer to obtain the hemp seed oil.

The method for extracting the extract of the mixture of *Mentha spicata* L. and *Cannabis sativa* L. was as follows: weighing and chopping 5 g of *Mentha spicata* L., adding it to the hemp seed oil obtained by the above method, soaking the resultant mixture for 2 h and then adding ethanol with a mass concentration of 50%, then extracting the resultant mixture for 3 times using microwave heating, filtering the resultant extract and concentrating the resultant filtrate under reduced pressure till no ethanol exists.

The methods for extracting various plant extracts in the component B and the air freshener composition were the same as those in Example 1.

Comparative Example 1

Comparative Example 1 was specifically the same as Example 4, except that the air freshener composition did not comprise the component A.

Comparative Example 2

Comparative Example 2 was specifically the same as Example 4, except that the air freshener composition did not comprise the component B.

Comparative Example 3

Comparative Example 3 was specifically the same as Example 4, except that the air freshener composition did not comprise the extract of the mixture of *Populus nigra* var. *italica*, grapefruit peels and eucalyptus leaves.

Comparative Example 4

Comparative Example 4 was specifically the same as Example 4, except that "the extract of the mixture of *Populus nigra* var. *italica*, grapefruit peels and eucalyptus leaves" was changed to "the extract of *Populus nigra* var. *italica*", wherein the extraction method of "the extract of *Populus nigra* var. *italica*" was the same as Example 1, except that grapefruit peels and eucalyptus leaves were not included.

Comparative Example 5

Comparative Example 5 was specifically the same as Example 4, except that "the extract of the mixture of *Populus nigra* var. *italica*, grapefruit peels and eucalyptus leaves" was changed to "the extract of *Populus nigra* var. *italica*", wherein the extraction method of "the extract of *Populus nigra* var. *italica*" was the same as Example 1, except that grapefruit peels and eucalyptus leaves were not included, and the *Populus nigra* var. *italica* leaves were changed to *Populus nigra* var. *italica* bark.

Comparative Example 6

Comparative Example 6 was specifically the same as Example 4, except that "the extract of the mixture of *Populus nigra* var. *italica*, grapefruit peels and eucalyptus leaves" was changed to "the extract of the mixture of *Populus nigra* var. *italica* and grapefruit peels", wherein the extraction method of "the extract of the mixture of *Populus nigra* var. *italica* and grapefruit peels" was the same as Example 1, except that eucalyptus leaves were not included.

Comparative Example 7

Comparative Example 7 was specifically the same as Example 4, except that "the extract of the mixture of *Populus nigra* var. *italica*, grapefruit peels and eucalyptus leaves" was changed to "the extract of the mixture of *Populus nigra* var. *italica* and eucalyptus leaves", wherein the extraction method of "the extract of the mixture of *Populus nigra* var. *italica* and eucalyptus leaves" was the same as Example 1, except that grapefruit peels were not included.

Comparative Example 8

Comparative Example 8 was specifically the same as Example 4, except that the "the extract of the mixture of *Mentha spicata* L. and *Cannabis sativa* L." was changed to the *Mentha spicata* L. extract.

The extraction method of the *Mentha spicata* L. extract was the same as Example 4, except that the hemp seed oil was not added.

Comparative Example 9

Comparative Example 9 was specifically the same as Example 4, except that "the extract of the mixture of *Mentha spicata* L. and *Cannabis sativa* L." was changed to the hemp seed oil.

The extraction method of the hemp seed oil was the same as Example 4.

Tests

The air freshener compositions prepared above were tested.

1. Test on duration of effectiveness of the air freshener compositions:

1.1. Fresh air freshener compositions.

In a 1 m3 sealed test chamber, a certain volume of chemically pure formaldehyde (or benzene or ammonia) was injected, and a fan in the chamber was turned on.

The gas concentration in the test chamber was sampled immediately after 1 hour as the initial concentration. In the 1 m3 sealed test chamber, the freshly prepared air freshener compositions were placed in the chamber. The gas concentrations in the test chamber were sampled immediately after 72 hours and used to calculate the removal rates. Removal rate=(initial concentration−sample concentration)×100/initial concentration. The test results are shown in Table 1.

1.2. The Air Freshener Compositions Stored for Two Months.

The specific experimental steps were the same as in 1.1, except that the air freshener compositions were used for the same test after being stored for two months. The test results are shown in Table 1.

In the table, TVOC is the total volatile organic compounds, i.e., all indoor organic gaseous substances.

Table 1. Test of the removal rates of the fresh air fresheners.

TABLE 1

Test of the removal rates of the fresh air fresheners.

| Examples | Removal rate of formaldehyde (%) | Removal rate of benzene (%) | Removal rate of ammonia | TVOC (removal) |
|---|---|---|---|---|
| Example 1 | 89.7 | 88.4 | 87.8 | 86.8 |
| Example 2 | 90.4 | 90.5 | 88.1 | 85.9 |
| Example 3 | 94.2 | 90.2 | 90.2 | 88.2 |
| Example 4 | 98.0 | 97.2 | 99.9 | 99.1 |
| Comparative Example 1 | 66.1 | 60.4 | 62.1 | 50.5 |
| Comparative Example 2 | 50.2 | 68.6 | 59.7 | 48.7 |
| Comparative Example 3 | 80.4 | 84.4 | 79.2 | 73.1 |
| Comparative Example 4 | 82.2 | 86.7 | 81.4 | 75.9 |
| Comparative Example 5 | 79.2 | 83.4 | 78.2 | 70.5 |
| Comparative Example 6 | 85.6 | 84.2 | 82.5 | 78.2 |
| Comparative Example 7 | 84.8 | 84.3 | 83.2 | 77.4 |
| Comparative Example 8 | 93.7 | 92.5 | 72.5 | 70.9 |
| Comparative Example 9 | 93.3 | 90.9 | 75.8 | 74.5 |

TABLE 2

Test of removal rates of the air freshener compositions stored for two months.

| Examples | Removal rate of formaldehyde (%) | Removal rate of benzene (%) | Removal rate of ammonia (%) | TVOC (removal) |
|---|---|---|---|---|
| Example 1 | 80.7 | 79.2 | 78.9 | 76.8 |
| Example 2 | 81.4 | 82.7 | 80.7 | 77.8 |
| Example 3 | 90.2 | 85.6 | 84.9 | 82.6 |
| Example 4 | 96.9 | 95.2 | 98.9 | 97.1 |
| Comparative Example 1 | 36.9 | 34.8 | 30.5 | 29.5 |
| Comparative Example 2 | 25.4 | 29.6 | 34.7 | 20.9 |
| Comparative Example 3 | 60.7 | 68.8 | 67.2 | 64.9 |
| Comparative Example 4 | 76.5 | 79.5 | 72.6 | 68.4 |
| Comparative Example 5 | 70.4 | 74.5 | 68.1 | 61.5 |
| Comparative Example 6 | 74.8 | 72.7 | 70.8 | 67.2 |
| Comparative Example 7 | 72.3 | 70.9 | 69.2 | 66.8 |
| Comparative Example 8 | 90.2 | 89.5 | 60.9 | 60.4 |
| Comparative Example 9 | 88.9 | 88.7 | 62.5 | 62.9 |

As can be seen in Tables 1 and 2, the air freshener composition obtained by preparation methods comprising a specific order and combined methods for extracting plant extracts has good removal effects on formaldehyde, benzene, ammonia and TVOC. Moreover, after being stored for two months, the air freshener composition of the present invention still has good removal effects on formaldehyde, benzene, ammonia and TVOC.

The foregoing examples are merely illustrative, and used to explain some of the features of the present disclosure. The appended claims are intended to claim the widest possible range that can be envisaged, and the examples presented herein are merely illustrative of the selected embodiments according to combinations of all possible examples. Accordingly, the applicants' intention is that the appended claims are not to be limited by the selected examples illustrative of the features of the present invention. Moreover, advances in technology will create possible equivalents or sub-substitutions that are not currently considered due to inaccuracies in language expression, and these changes should also be construed as covered by the appended claims wherever possible.

The invention claimed is:

1. An air freshener composition, comprising component A and component B, wherein a weight ratio of the component A to the component B is 1:0.5-3;
   the component A comprises, in parts by weight, 10-30 parts by weight of an active agent, 6-15 parts by weight of a carrier, 1-4 parts by weight of a pH regulator, and 0.01-0.2 part by weight of an antioxidant;
   the active agent comprises a compound containing at least two hydroxyl groups; and the carrier comprises an organic acid having 16-24 carbon atoms; and
   the component B is a plant extract solution, wherein the plant extract solution comprises at least, in parts by weight: 5-30 parts by weight of an extract of a mixture of *Populus nigra* var. *italica*, grapefruit peels and eucalyptus leaves; 0.1-5 parts by weight of *Sophora flavescens* extract; 1-3 parts by weight of *Aloe vera* extract; 1-10 parts by weight of fresh orange peel extract; 0.5-3 parts by weight of *Nandina domestica* extract; 0.5-10 parts by weight of *Eucalyptus robusta* Smith extract; 1-8 parts by weight of *Robinia pseudoacacia* L. extract; 1-5 parts by weight of *Chrysanthemum morifolium* extract, and 0.1-2 parts by weight of artemisinin.

2. The air freshener composition according to claim 1, comprises component A and component B, wherein a weight ratio of the component A to the component B is 1:1-3;
   the component A comprises, in parts by weight, 18-28 parts by weight of an active agent, 8-12 parts by weight of a carrier, 2-3 parts by weight of the pH regulator, and 0.1-0.2 part by weight of the antioxidant;
   the active agent comprises a compound containing at least two hydroxyl groups; and the carrier comprises an organic acid having 16-24 carbon atoms; and
   the component B is a plant extract solution, wherein the plant extract solution comprises at least, in parts by weight: 15-28 parts by weight of an extract of a mixture of *Populus nigra* var. *italica*, grapefruit peels and eucalyptus leaves; 1-3 parts by weight of *Sophora flavescens* extract; 1.5-3 parts by weight of *Aloe vera* extract; 3-8 parts by weight of fresh orange peel extract; 1-2 parts by weight of *Nandina domestica* extract; 3-10 parts by weight of *Eucalyptus robusta* Smith extract; 2-6 parts by weight of *Robinia pseudoacacia* L. extract; 2-4 parts by weight of *Chrysanthemum morifolium* extract; and 0.5-1.5 parts by weight of artemisinin.

3. The air freshener composition according to claim 2, comprises component A and component B, wherein the weight ratio of the component A to the component B is 1:2;
   the component A comprises, in parts by weight, 25 parts by weight of an active agent, 10 parts by weight of a carrier, 2.5 parts by weight of the pH regulator and 0.1 part by weight of the antioxidant;
   the active agent comprises a compound containing at least two hydroxyl groups; and the carrier comprises an organic acid having 16-24 carbon atoms; and
   the component B is a plant extract solution, wherein the plant extract solution comprises at least, in parts by weight: 25 parts by weight of an extract of a mixture of *Populus nigra* var. *italica*, grapefruit peels and eucalyptus leaves; 2 parts by weight of *Sophora flavescens* extract; 3 parts by weight of *Aloe vera* extract; 7 parts by weight of fresh orange peel extract; 1.5 parts by weight of *Nandina domestica* extract; 8 parts by weight of *Eucalyptus robusta* Smith extract; 5 parts by weight of *Robinia pseudoacacia* L. extract; 4 parts by weight of *Chrysanthemum morifolium* extract; and 1 part by weight of artemisinin.

4. The air freshener composition according to claim 1, wherein the active agent is selected from a combination of any one or more of ethylene glycol, propylene glycol, butylene glycol, polyethylene glycol, glycerol and 1,3,5-cyclohexanetriol.

5. The air freshener composition according to claim 1, wherein the carrier is selected from a combination of any one or more of palmitic acid, stearic acid, arachidic acid and behenic acid.

6. The air freshener composition according to claim 1, wherein a method for extracting the extract of the mixture of *Populus nigra* var. *italica*, grapefruit peels and eucalyptus leaves is as follows:
   weighing and then crushing dried *Populus nigra* var. *italica* leaves, grapefruit peels and eucalyptus leaves at a weight ratio of 10:5:2, adding ethanol with a mass fraction of 95%, extracting a resultant mixture for 2-3 times using microwave heating after soaking for 3-10 h, filtering a resultant extract, and concentrating a resultant filtrate under reduced pressure till no ethanol exists.

7. The air freshener composition according to claim 1, wherein a method for extracting the *Nandina domestica* extract is as follows:

after weighing and then crushing dried *Nandina domestica*, soaking resultant powder with white vinegar for 1-3 h, then adding 60% ethanol, extracting a resultant mixture for 2-3 times using microwave heating after soaking for 2-5 h, filtering a resultant extract and concentrating a resultant filtrate under reduced pressure till no white vinegar and ethanol exist.

8. The air freshener composition according to claim 1, wherein the component B further comprises 1 part by weight of an extract of a mixture of *Mentha spicata* L. and *Cannabis sativa* L.

9. An air freshener product comprising the air freshener composition according to claim 1.

10. The air freshener product according to claim 9, wherein the air freshener composition comprises component A and component B, wherein a weight ratio of the component A to the component B is 1:1-3;

the component A comprises, in parts by weight, 18-28 parts by weight of an active agent, 8-12 parts by weight of a carrier, 2-3 parts by weight of the pH regulator, and 0.1-0.2 part by weight of the antioxidant;

the active agent comprises a compound containing at least two hydroxyl groups; and the carrier comprises an organic acid having 16-24 carbon atoms; and the component B is a plant extract solution, wherein the plant extract solution comprises at least, in parts by weight: 15-28 parts by weight of an extract of a mixture of *Populus nigra* var. *italica*, grapefruit peels and eucalyptus leaves; 1-3 parts by weight of *Sophora flavescens* extract; 1.5-3 parts by weight of *Aloe vera* extract; 3-8 parts by weight of fresh orange peel extract; 1-2 parts by weight of *Nandina domestica* extract; 3-10 parts by weight of *Eucalyptus robusta* Smith extract; 2-6 parts by weight of *Robinia pseudoacacia* L. extract; 2-4 parts by weight of *Chrysanthemum morifolium* extract; and 0.5-1.5 parts by weight of artemisinin.

11. The air freshener product according to claim 10, wherein the air freshener composition comprises component A and component B, wherein the weight ratio of the component A to the component B is 1:2;

the component A comprises, in parts by weight, 25 parts by weight of an active agent, 10 parts by weight of a carrier, 2.5 parts by weight of the pH regulator and 0.1 part by weight of the antioxidant;

the active agent comprises a compound containing at least two hydroxyl groups; and the carrier comprises an organic acid having 16-24 carbon atoms; and the component B is a plant extract solution, wherein the plant extract solution comprises at least, in parts by weight: 25 parts by weight of an extract of a mixture of *Populus nigra* var. *italica*, grapefruit peels and eucalyptus leaves; 2 parts by weight of *Sophora flavescens* extract; 3 parts by weight of *Aloe vera* extract; 7 parts by weight of fresh orange peel extract; 1.5 parts by weight of *Nandina domestica* extract; 8 parts by weight of *Eucalyptus robusta* Smith extract; 5 parts by weight of *Robinia pseudoacacia* L. extract; 4 parts by weight of *Chrysanthemum morifolium* extract; and 1 part by weight of artemisinin.

12. The air freshener product according to claim 9, wherein the active agent is selected from a combination of any one or more of ethylene glycol, propylene glycol, butylene glycol, polyethylene glycol, glycerol and 1,3,5-cyclohexanetriol.

13. The air freshener product according to claim 9, wherein the carrier is selected from a combination of any one or more of palmitic acid, stearic acid, arachidic acid and behenic acid.

14. The air freshener product according to claim 9, wherein a method for extracting the extract of the mixture of *Populus nigra* var. *italica*, grapefruit peels and eucalyptus leaves is as follows:

weighing and then crushing dried *Populus nigra* var. *italica* leaves, grapefruit peels and eucalyptus leaves at a weight ratio of 10:5:2, adding ethanol with a mass fraction of 95%, extracting a resultant mixture for 2-3 times using microwave heating after soaking for 3-10 h, filtering a resultant extract, and concentrating a resultant filtrate under reduced pressure till no ethanol exists.

15. The air freshener product according to claim 9, wherein a method for extracting the *Nandina domestica* extract is as follows:

after weighing and then crushing dried *Nandina domestica*, soaking resultant powder with white vinegar for 1-3 h, then adding 60% ethanol, extracting a resultant mixture for 2-3 times using microwave heating after soaking for 2-5 h, filtering a resultant extract and concentrating a resultant filtrate under reduced pressure till no white vinegar and ethanol exist.

16. The air freshener product according to claim 9, wherein the component B further comprises 1 part by weight of an extract of a mixture of *Mentha spicata* L. and *Cannabis sativa* L.

* * * * *